US006843961B2

(12) United States Patent
Hlavinka et al.

(10) Patent No.: US 6,843,961 B2
(45) Date of Patent: *Jan. 18, 2005

(54) REDUCTION OF CONTAMINANTS IN BLOOD AND BLOOD PRODUCTS USING PHOTOSENSITIZERS AND PEAK WAVELENGTHS OF LIGHT

(75) Inventors: Dennis J. Hlavinka, Arvada, CO (US); Raymond P. Goodrich, Lakewood, CO (US); Laura Goodrich, Lakewood, CO (US); Daniel McGraw, Riverton, UT (US)

(73) Assignee: Gambro, Inc., Lakewood, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/357,599

(22) Filed: Feb. 3, 2003

(65) Prior Publication Data

US 2003/0219354 A1 Nov. 27, 2003

Related U.S. Application Data

(63) Continuation-in-part of application No. 09/962,029, filed on Sep. 25, 2001, which is a continuation-in-part of application No. 09/596,429, filed on Jun. 15, 2000.
(60) Provisional application No. 60/235,999, filed on Sep. 27, 2000, and provisional application No. 60/353,223, filed on Feb. 1, 2002.

(51) Int. Cl.[7] .............................. A61L 2/00; B01J 19/00; C12N 13/00; C12N 1/00; C12N 9/00
(52) U.S. Cl. ............................... 422/24; 422/1; 422/22; 422/28; 422/40; 422/44; 422/292; 422/307; 435/448; 435/173.1; 435/183; 435/184; 435/236; 435/243; 435/244
(58) Field of Search ...................... 422/1, 3, 22, 24, 422/28, 32, 40, 44, 292, 307; 435/448, 173.1, 183–184, 236, 243, 244

(56) References Cited

U.S. PATENT DOCUMENTS

| 4,167,669 A | 9/1979 | Panico ........................ 250/341 |
|---|---|---|
| 4,336,809 A | 6/1982 | Clark .......................... 128/665 |
| 4,464,336 A | 8/1984 | Hiramoto ..................... 422/24 |
| 4,614,190 A | 9/1986 | Stanco et al. ............... 128/395 |
| 4,726,949 A | 2/1988 | Miripol et al. ............ 324/65 R |
| 4,727,027 A | 2/1988 | Wiesehahn et al. ......... 424/101 |
| 4,866,282 A | 9/1989 | Miripol et al. .............. 435/173 |
| 4,871,559 A | 10/1989 | Dunn et al. ............. 250/455.1 |
| 4,880,512 A | 11/1989 | Cornelius et al. ........... 426/248 |
| 4,910,942 A | 3/1990 | Dunn et al. ............ 204/157.61 |
| 4,952,812 A | 8/1990 | Miripol et al. ................ 53/425 |

(List continued on next page.)

FOREIGN PATENT DOCUMENTS

| DE | 42 35 841 | 4/1994 |
|---|---|---|
| EP | 0 525138 | 9/1998 |
| GB | 2212010 | 7/1989 |

(List continued on next page.)

OTHER PUBLICATIONS

Ser. application No. 09/596,429.*
Andreu, et al, "Ultraviolet irradiation of platelet concentrates: feasibility in transfusion practice", *Transfusion*, v. 30, No. 5, 1990 pp 401–406.
Golding et al, "Eradication of bacterial species via photosensitization", SPIE, vo. 3563, 9/98, pp 18–27.

(List continued on next page.)

*Primary Examiner*—Terrence R. Till
*Assistant Examiner*—Monzer R. Chorbaji
(74) *Attorney, Agent, or Firm*—Laura M. Butterfield; Edna M. O'Connor; John R. Merkling

(57) ABSTRACT

Methods and apparatuses are provided for inactivation of pathogens in fluids containing blood products. Preferred methods include the steps of adding an effective, nontoxic amount of a photosensitizer such as riboflavin to the blood product and exposing the fluid to light having a peak wavelength.

38 Claims, 15 Drawing Sheets

U.S. PATENT DOCUMENTS

| | | | |
|---|---|---|---|
| 5,034,235 A | 7/1991 | Dunn et al. | 426/238 |
| 5,235,045 A | 8/1993 | Lewis et al. | 534/560 |
| 5,290,221 A | 3/1994 | Wolf, Jr. et al. | 604/4 |
| 5,300,019 A | 4/1994 | Bischof et al. | 604/4 |
| 5,427,920 A | 6/1995 | Berndt et al. | 501/103 |
| 5,484,778 A | 1/1996 | Kenney et al. | 514/63 |
| 5,489,442 A | 2/1996 | Dunn et al. | 426/248 |
| 5,527,704 A | 6/1996 | Wolf, Jr. et al. | 435/283.1 |
| 5,547,635 A | 8/1996 | Duthie et al. | 422/24 |
| 5,624,435 A | 4/1997 | Furumoto et al. | 606/10 |
| 5,658,530 A | 8/1997 | Dunn | 422/24 |
| 5,658,722 A | 8/1997 | Margolis-Nunno et al. | 435/2 |
| 5,688,475 A | 11/1997 | Duthie, Jr. | 422/186.3 |
| 5,698,866 A | 12/1997 | Doiron et al. | 257/99 |
| 5,762,867 A | 6/1998 | D'Silva | 422/44 |
| 5,768,853 A | 6/1998 | Bushnell et al. | 53/167 |
| 5,786,598 A | 7/1998 | Clark et al. | 250/455.11 |
| 5,798,523 A | 8/1998 | Villeneuve et al. | 250/234 |
| 5,868,695 A | 2/1999 | Wolf, Jr. et al. | 604/4 |
| 5,900,211 A | 5/1999 | Dunn et al. | 422/24 |
| 5,922,278 A | 7/1999 | Chapman et al. | 422/22 |
| 5,925,885 A | 7/1999 | Clark et al. | 250/492.1 |
| 5,951,509 A | 9/1999 | Morris | 604/4 |
| 6,004,741 A | 12/1999 | Wollowitz et al. | 435/2 |
| 6,013,918 A | 1/2000 | Bushnell et al. | 250/454.11 |
| 6,054,097 A | 4/2000 | Mass et al. | 422/24 |
| 6,158,319 A | 12/2000 | D'Silva | 83/397 |
| 6,165,711 A | 12/2000 | Dorner et al. | 435/5 |
| 6,228,332 B1 | 5/2001 | Dunn et al. | 422/186.3 |
| 6,258,577 B1 * | 7/2001 | Goodrich et al. | 435/173.3 |
| 6,261,518 B1 | 7/2001 | Caputo et al. | 422/22 |
| 6,268,120 B1 * | 7/2001 | Platz et al. | 435/2 |
| 6,312,931 B1 * | 11/2001 | O'Dwyer et al. | 435/173.1 |

FOREIGN PATENT DOCUMENTS

| | | |
|---|---|---|
| WO | WO92/11057 | 7/1992 |
| WO | WO93/21992 | 11/1993 |
| WO | WO95/02325 | 1/1995 |
| WO | WO96/06647 | 3/1996 |
| WO | WO99/59645 | 11/1999 |
| WO | WO00/47240 | 8/2000 |
| WO | WO00/74731 | 12/2000 |
| WO | WO01/23007 | 4/2001 |

OTHER PUBLICATIONS

Johnston et al, "Low–level Psoralen–deoxyribonucleic Acid Cross–links induced by Single Laser Pulses", *Biochemistry*, 1981, 20, 739–745.

Lytle et al,"Light Emitting Diode Source for Photodynamic Therapy", SPIE, vol. 1881, *Optical Methods for Tumor Treatment and Detection*, 1993, pp. 180–188.

Pamphilon et al, "Platelet concentrates irradiated with ultra-violet light retain satisfactory in vitro storag characteristics and in vivo survival", *British J. of Haematology*, 1990, 75, 240–244.

Prodouz et al, "Use of Laser–UV for Inactivation of Virus in Blood Products", *Blood*, vol. 70 No 2, Aug. 1987, pp 589–592.

Snyder et al, "Storage of platelet concentrates after high-–dose ultraviolet B irradiation", *Transfusion*, vo. 31, No. 6, 1991, pp491–496.

Zhizhina et al, "Formation of free radicals and DNA breaks after pulsed laser irradiation of DNA complexes with intercalating dyes", *Biofizika*, vol. 35, n 1, Jan.–Feb., 1990, pp 47–52 (abstract nly).

* cited by examiner

REDUCTION OF CONTAMINANTS IN BLOOD AND BLOOD PRODUCTS USING PHOTOSENSITIZERS AND PEAK WAVELENGTHS OF LIGHT

This application is a Continuation-In-Part of U.S. application Ser. Nos. 09/962,029 filed Sep. 25, 2001, 09/596,429 filed Jun. 15, 2000. application Ser. No. 09/962,029 claims benefit of U.S. Provisional Application 60/235,999 filed Sep. 27, 2000. This Application also claims the benefit of U.S. Provisional Application No. 60/353,223 filed Feb. 1, 2002.

BACKGROUND

Contamination of whole blood or blood products with infectious microorganisms such as HIV, hepatitis and other viruses and bacteria present a serious health hazard for those who must receive transfusions of whole blood or administration of various blood products or blood components such as platelets, red cells, blood plasma, Factor VIII, plasminogen, fibronectin, anti-thrombin III, cryoprecipitate, human plasma protein fraction, albumin, immune serum globulin, prothrombin complex plasma growth hormones, and other components isolated from blood. Blood screening procedures may miss pathogenic contaminants, and sterilization procedures which do not damage cellular blood components but effectively inactivate all infectious viruses and other microorganisms have not heretofore been available.

The use of pathogen inactivating agents include certain photosensitizers, or compounds which absorb light of defined wavelengths and transfer the absorbed energy to an energy acceptor, have been proposed for inactivation of microorganisms found in blood products or fluids containing blood products. Such photosensitizers may be added to the fluid containing blood or blood products and irradiated.

The photosensitizers which may be used in this invention include any photosensitizers known to the art to be useful for inactivating microorganisms. A "photosensitizer" is defined as any compound which absorbs radiation at one or more defined wavelengths and subsequently utilizes the absorbed energy to carry out a chemical process. Examples of photosensitizers which may be used for the reduction of pathogens in blood or blood products include porphyrins, psoralens, dyes such as neutral red, methylene blue, acridine, toluidines, flavine (acriflavine hydrochloride) and phenothiazine derivatives, coumarins, quinolones, quinones, and anthroquinones.

A number of systems and methods for irradiating pathogens in a fluid with light either with or without the addition of a photosensitizer are known in the art. For example, U.S. Pat. No. 5,762,867 is directed toward a system for activating a photoactive agent present in a body fluid with light emitting diodes (LEDs).

U.S. Pat. No. 5,527,704 is directed toward an apparatus containing LEDs used to activate a fluid containing methylene blue.

U.S. Pat. No. 5,868,695 discloses using LEDs having a red color and emitting light at a wavelength of 690 nm in combination with benzoporphrin derivative photosensitizers to inactivate red blood cells. As taught in this patent, at a wavelength of 690 nm, red blood cells are essentially transparent to radiation, and as such, the benzoporphorin derivatives absorb radiation at this wavelength to become activated. Also disclosed in this patent is the use of LEDs having a blue color and emitting light at a peak wavelength of 425 nm to inactivate platelets.

U.S. Pat. No. 5,658,722 discloses irradiating platelets using UVA1 light having an emission peak near 365 nm. This patent teaches that damage to platelets is caused by short UVA<345 nm, and unlike the present invention, calls for removing UVA wavelengths below 345 nm.

Use of light which is variably pulsed at a wavelength of 308 nm without the addition of a photosensitizer to inactivate virus in a washed platelet product is taught in an article by Prodouz et al. (Use of Laser-UV for Inactivation of Virus in Blood Products; Kristina Prodouz, Joseph Fratantoni, Elizabeth Boone and Robert Bonner; Blood, Vol 70, No. 2). This article does not teach or suggest the addition of a photosensitizer in combination with light to kill viruses.

The present invention is directed toward the reduction of pathogens which may be present in blood or blood products using light having peak wavelengths in combination with an endogenous photosensitizer.

SUMMARY

The present invention provides a method and apparatus for irradiating a fluid containing blood products and pathogens, together with a photoactive agent. The fluid is exposed to light having a peak wavelength which is chosen to activate both the photoactive agent as well as to penetrate the fluid containing the specific blood product to inactivate any pathogens contained in the fluid.

One embodiment useful with the methods of the present invention is a radiation or treatment chamber having includes a bank or banks or arrays of lights, which emit light at an approximate peak wavelength of 470 nm, which is suitable for irradiating a red blood cell product.

Another embodiment of the present invention includes use of light emitted at an approximate peak wavelength of 308 nm, which is suitable for irradiating a platelet or plasma product.

A radiation enhancer such as a second radiation source or a reflective surface may be included in the radiation or treatment chamber. The radiation enhancer may be placed adjacent to the container containing the fluid to be irradiated or opposite the radiation source to increase the amount of radiation contacting the fluid within the container.

The radiation or treatment chamber may also preferably include a means for producing movement in the fluid to be irradiated. Movement provides many benefits including improvement of the efficiency of the irradiation process by helping mix the photosensitizer with the fluid to be pathogen inactivated to provide turnover of the fluid within the container at the container-light interface.

Positioning the fluid to be irradiated so that it receives energy of sufficient wavelength and power to reduce pathogens contained in the fluid may include a support platform, a shelf or a tray for the sample to be disposed upon; an opening or gap between two supports which may be a light or light arrays, where the fluid within the container is positioned between the supports; or other means known in the art. The support platform may move in a substantially horizontal manner as in a conveyer line, or may oscillate or agitate. A support platform which may move in a substantially vertical plane or any angle therebetween may also be used. The fluid-holding support platform or surface may be transparent to one or more of the wavelengths of light applied. The fluid within the container may also be placed on the support surface between two or more sources of radiation, in a sandwich-like configuration.

Alternative sources of radiation may be used, depending on a variety of factors, including, but not limited to the type of fluid being irradiated and the type of photosensitizer being used.

DETAILED DESCRIPTION

Figure 1:
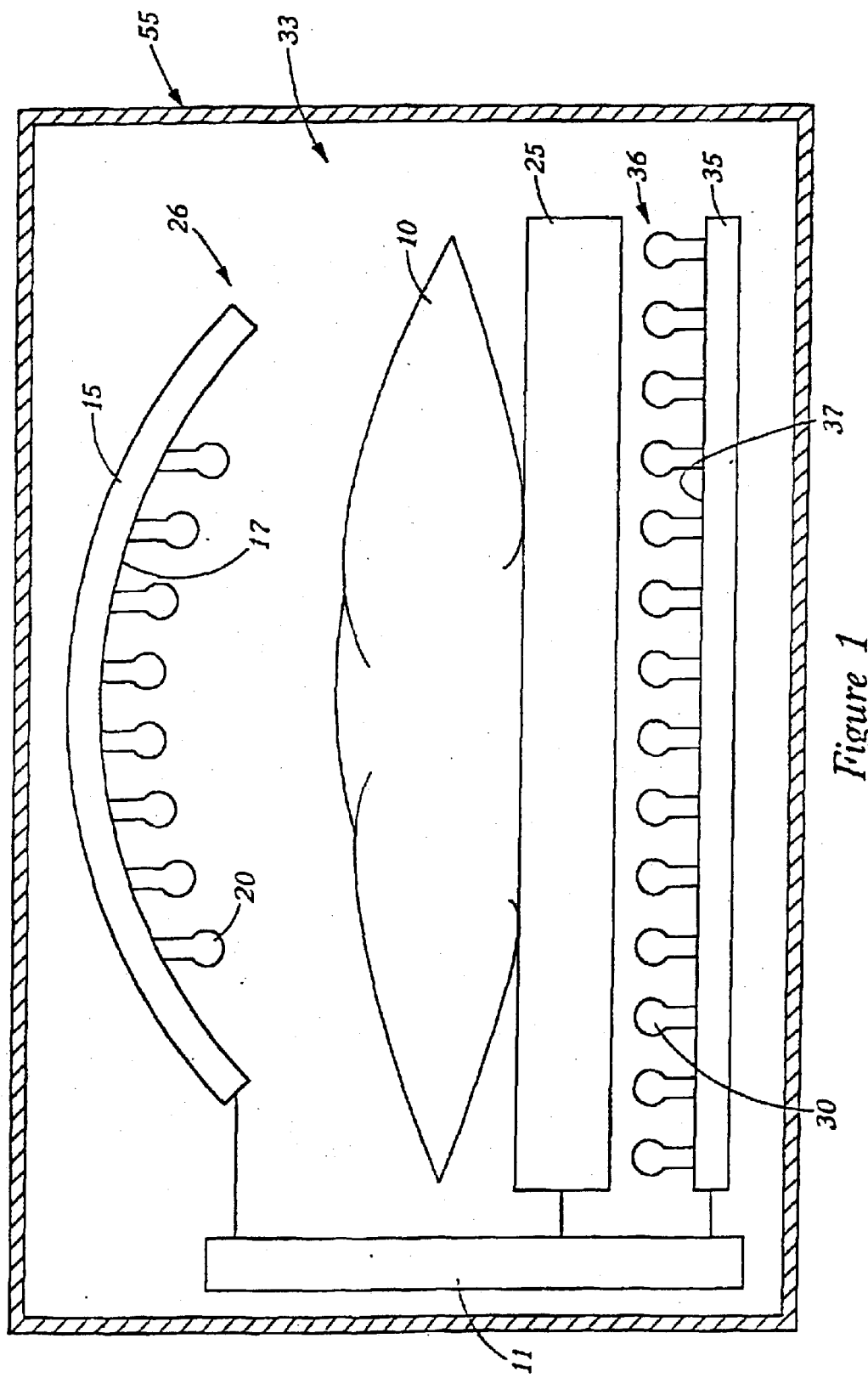
FIG. 1 is a cross-sectional view of a treatment chamber which may be used in the present invention.

The term "blood product" as used herein includes all blood constituents or blood components and therapeutic protein compositions containing proteins derived from blood as described above. Fluids containing biologically active proteins other than those derived from blood may also be treated by the methods and devices of this invention.

Photosensitizers of this invention may include compounds which preferentially adsorb to nucleic acids, thus focusing their photodynamic effect upon microorganisms and viruses with little or no effect upon accompanying cells or proteins. Other types of photosensitizers are also useful in this invention, such as those using singlet oxygen-dependent mechanisms.

Most preferred are endogenous photosensitizers. The term "endogenous" means naturally found in a human or mammalian body, either as a result of synthesis by the body or by ingestion as an essential foodstuff (e.g. vitamins) or formation of metabolites and/or byproducts in vivo. Examples of such endogenous photosensitizers are alloxazines such as 7,8-dimethyl-10-ribityl isoalloxazine (riboflavin), 7,8,10-trimethylisoalloxazine (lumiflavin), 7,8-dimethylalloxazine (lumichrome), isoalloxazine-adenine dinucleotide (flavine adenine dinucleotide [FAD]), alloxazine mononucleotide (also known as flavine mononucleotide [FMN] and riboflavine-5-phosphate), vitamin Ks, vitamin L, their metabolites and precursors, and napththoquinones, naphthalenes, naphthols and their derivatives having planar molecular conformations. The term "alloxazine" includes isoalloxazines. Endogenously-based derivative photosensitizers include synthetically derived analogs and homologs of endogenous photosensitizers which may have or lack lower (1–5) alkyl or halogen substituents of the photosensitizers from which they are derived, and which preserve the function and substantial non-toxicity thereof. When endogenous photosensitizers are used, particularly when such photosensitizers are not inherently toxic or do not yield toxic photoproducts after photoradiation, no removal or purification step is required after decontamination, and a treated product can be directly returned to a patient's body or administered to a patient in need of its therapeutic effect without any further required processing. Using endogenous photosensitizers to inactivate pathogens in a blood product are described in U.S. Pat. Nos. 6,258,577 and 6,277,337, herein incorporated by reference in their entirety to the amount not inconsistent.

Non-endogenous photosensitizers based on endogenous structures, such as those described in U.S. Pat. No. 6,268,120, may also be used in the present invention, and is incorporated by reference herein. These non-endogenous photosensitizers and endogenously-based derivative photosensitizers may be referred to herein as endogenously-based derivative photosensitizers.

One mechanism by which these photosensitizers may inactivate pathogens is by interfering with nucleic acids, so as to prevent replication of the nucleic acid. As used herein, the term "inactivation of a pathogen" means totally or partially preventing the pathogen from replicating, either by killing the pathogen or otherwise interfering with its ability to reproduce. Specificity of action of the preferred photosensitizer is conferred by the close proximity of the photosensitizer to the nucleic acid of the pathogen and this may result from binding of the photosensitizer to the nucleic acid. "Nucleic acid" includes ribonucleic acid (RNA) and deoxyribonucleic acid (DNA). It should be noted however, photosensitizers may be used in this invention which have mechanisms of action different from those described for endogenous photosensitizers or endogenously-based derivative photosensitizers. For example, photosensitizers which bind to membranes may also be used.

Upon exposure of the photosensitizer to light of a particular wavelength, the photosensitizer will absorb the light energy, causing photolysis of the photosensitizer and any nucleic acid bound to the photosensitizer. In this invention, the photosensitizer used in the examples is 7,8-dimethyl-10-ribityl isoalloxazine (riboflavin).

Microorganisms or pathogens which may be eradicated or inactivated using pathogen inactivation agents or photosensitizers include, but are not limited to, viruses (both extracellular and intracellular), bacteria, bacteriophages, fungi, blood-transmitted parasites, and protozoa. Exemplary viruses include acquired immunodeficiency (HIV) virus, hepatitis A, B and C viruses, sinbis virus, cytomegalovirus, vesicular stomatitis virus, herpes simplex viruses, e.g. types I and II, human T-lymphotropic retroviruses, HTLV-III, lymphadenopathy virus LAV/IDAV, parvovirus, transfusion-transmitted (TT) virus, Epstein-Barr virus, and others known to the art. Bacteriophages include Φ X174, Φ 6, λ, R17, $T_4$, and $T_2$. Exemplary bacteria include but are not limited to *P. aeruginosa, S. aureus, S. epidermis, L. monocytogenes, E. coli, K. pneumonia* and *S. marcescens*.

The fluid to be pathogen inactivated has the photosensitizer added thereto, and the resulting fluid mixture may be exposed to photoradiation of the appropriate peak wavelength and amount to activate the photosensitizer, but less than that which would cause significant non-specific damage to the biological components or substantially interfere with biological activity of other proteins present in the fluid.

The term peak wavelength as defined herein means that the light is emitted in a narrow range centered around a wavelength having a particular peak intensity. In one embodiment, visible light may be centered around a wavelength of approximately 470 nm, and having a maximum intensity at approximately 470 nm. In another embodiment, the light may be centered around a narrow range of UV light at an approximate wavelength of 308 nm, and having a maximum intensity at approximately 308 nm. The term light source or radiation source as defined herein means an emitter of radiant energy, and may include energy in the visible and/or ultraviolet range, as further described below.

The photosensitizer may be added directly to the fluid to be pathogen inactivated, or may be flowed into the photopermeable container separately from the fluid being treated, or may be added to the fluid prior to placing the fluid in the photopermeable treatment container. The photosensitizer may also be added to the photopermeable container either before or after sterilization of the treatment container.

The fluid containing the photosensitizer may also be flowed into and through a photopermeable container for irradiation, using a flow through type system. Alternatively, the fluid to be treated may be placed in a photopermeable container which is agitated and exposed to photoradiation for a time sufficient to substantially inactivate the microorganisms, in a batch-wise type system.

The term "container" refers to a closed or open space, which may be made of rigid or flexible material, e.g., may be a bag or box or trough. In one embodiment, the container may be closed or open at the top and may have openings at both ends, e.g., may be a tube or tubing, to allow for flow-through of fluid therein. A cuvette has been used to exemplify one embodiment of the invention involving a flow-through system. Collection bags, such as those used with the Trima® and/or Spectra™ apheresis systems of Gambro, Inc., (f/k/a Cobe Laboratories, Inc., Lakewood, Colo., USA), have been used to exemplify another embodiment involving a batch-wise treatment of the fluid.

The term "photopermeable" means the material of the treatment container is adequately transparent to photoradiation of the proper wavelength for activating the photosensitizer. In a flow-through system, the container has a depth (dimension measured in the direction of the radiation from the photoradiation source) sufficient to allow photoradiation to adequately penetrate the container to contact photosensitizer molecules at all distances from the light source and ensure inactivation of pathogens in the fluid to be decontaminated, and a length (dimension in the direction of fluid flow) sufficient to ensure a sufficient exposure time of the fluid to the photoradiation. The materials for making such containers, as well as the depths and lengths of the containers may be easily determined by those skilled in the art, and together with the flow rate of fluid through the container, the intensity of the photoradiation and the absorptivities of the fluid components, e.g., plasma, platelets, red blood cells, will determine the amount of time the fluid should be exposed to photoradiation. The container used may be any container known in the art for holding fluid to be irradiated, including, but not limited to blood bags, cuvettes and tubing. One example, not meant to be limiting which may be used as the container is a Sangewald bag (available from Sengewald Verpackungen GmbH & Co. KG).

After treatment, the blood or blood product may be stored for later delivery to a patient, concentrated, infused directly into a patient or otherwise processed for its ultimate use.

FIG. 1 shows in a cross-sectional view, the inside of a radiation or treatment chamber of one type of apparatus that may be used in the present invention. The treatment chamber shown in FIG. 1 may be used in batch-wise systems, however, it should be noted that similar elements may also be used in flow-through systems. It should be noted that throughout the description of the invention, like elements have been given like numerals. The apparatus 55, used for inactivating a fluid which may contain pathogens, consists of an internal chamber 33 having at least one source of radiation 26. In one preferred embodiment, the internal chamber may contain a second source of radiation 36. Each radiation source 26 and 36 respectively, is depicted as including a plurality of discrete radiation-emitting elements. The internal chamber 33 further consists of a support platform 25 for supporting the fluid container 10 containing the fluid to be irradiated, and a control unit 11.

As introduced above, two sources of radiation are shown within internal chamber 33. Radiation source 26 may be located along the top portion of the internal chamber 33 above the container 10 which holds or contains the fluid to be irradiated, while radiation source 36 may be located along the bottom portion of the internal chamber 33 below the container 10. Although not shown, radiation sources may also be located along some or all of the sides of the internal chamber 33 perpendicular to the container 10. The radiation or treatment chamber 55 may alternatively contain a single radiation source at any location within the internal chamber 33 and still comply with the spirit and scope of the present invention.

The radiation source including a plurality of radiation-emitting elements collectively designated as source 26 includes an upper support substrate 15 containing a plurality of discrete radiation emitting elements or discrete light sources (see discrete source 20 as one example) mounted thereon. The support substrate 15 may be in an arcuate shape as shown, in a flat shape, or in other configurations which are not shown but are known in the art. Thus, the upper support substrate 15 could also be in a shape other than arcuate without departing from the spirit and scope of the invention.

As further depicted in FIG. 1, the radiation source collectively designated as discrete source 36 includes a lower support substrate 35 which also contains a plurality of discrete radiation emitting elements or discrete light sources (see discrete source 30 as another example). Lower support substrate 35 preferably runs parallel to support platform 25. The lower support substrate 35 may be substantially flat as shown, or may be in an arcuate shape similar to element 15 above, or may be in a shape other than arcuate, without departing from the spirit and scope of the invention.

As shown in FIG. 1, the support substrates 15 and 35 may include at least one reflective surface, and as shown, may include two or more reflective surfaces 17 and 37 thereon. Reflective surface 17 is shown as running contiguous with upper support substrate 15. Reflective surface 37 is shown as running contiguous with lower support substrate 35. The reflective surfaces 17 and 37 may also run contiguously with only a portion of support substrates 15 and 35. As shown in FIG. 1, discrete light source devices 20 and 30 extend outwardly away from the surface of the support substrates 15 and 35. Alternatively, a discrete light source could be recessed into the surface such that the surface surrounds each discrete light source in a parabolic shape (not shown).

Figure 2:
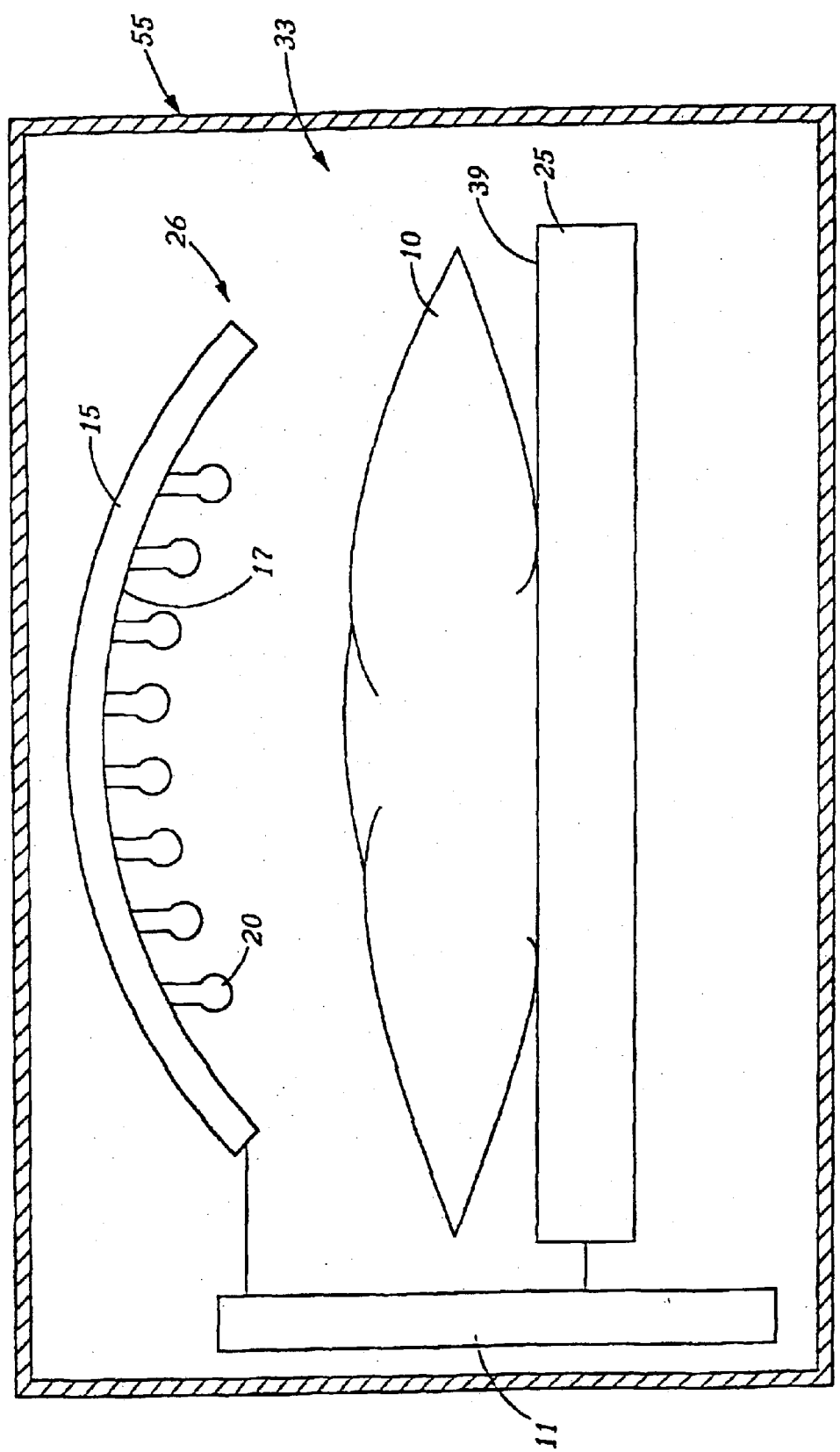
FIG. 2 is a cross-sectional view of a treatment chamber like that of FIG. 1, but with an alternative reflective surface that may also be used in the present invention.

The support substrate may or may not have reflective surfaces. In a further alternative configuration, the reflective surface may not contain any light sources. Such a reflective surface containing no light sources (not shown) may be located within the treatment chamber on a side opposite from the radiation source. As shown in FIG. 2, the support platform 25 may have a reflective surface 39. This reflective surface 39 on support platform 25 may be in place of, or may be in addition to another reflective surface (see element 17 as one example) within the treatment chamber. There may also be no reflective surfaces at all within the treatment chamber.

In any of these reflective surface embodiments, the reflective surface may be coated with a highly reflective material which serves to reflect the radiation emitted from the lights back and forth throughout the treatment chamber until the radiation is preferably completely absorbed by the fluid being irradiated. The highly reflective nature of the reflective surface reflects the emitted light back at the fluid-filled bag or container 10 with minimum reduction in the light intensity.

In FIG. 1, support platform 25 is positioned within the internal treatment chamber 33. The support platform 25 may be located substantially in the center of the radiation or treatment chamber (as shown in FIG. 1), or may be located closer to either the top portion or the bottom portion of the treatment chamber without departing from the spirit and scope of the present invention. The support platform 25 supports the container 10 containing the fluid to be irradiated. The support platform 25 may also be defined as a tray or a shelf. Additionally or alternatively, the platform 25 may be made of a photopermeable material to enable radiation emitted by the lights to be transmitted through the platform and penetrate the fluid contained within the container 10. The platform may also be a wire or other similar mesh-like material to allow maximum light transmissivity therethrough.

The support platform 25 is preferably capable of movement in multiple directions within the treatment chamber. One type of agitator, such as a Helmer flatbed agitation system available from Helmer Corp. (Noblesville, Ind., USA) may be used. This type of agitator provides to and fro motion. Other types of agitators may also be used to provide a range of motion to the fluid contained within the container 10, without departing from the spirit and scope of the invention. For example, the support platform might be oriented in a vertical direction and the light sources may be rotated about a horizontal axis. The support platform 25 may alternatively rotate in multiple possible directions within the radiation chamber in varying degrees from between 0° to 360°. Support platform 25 may also oscillate back and forth, or side to side along the same plane. As a further alternative, one or more of the light sources may also move in a coordinated manner with the movement of the support platform. Such oscillation or rotation would enable the majority of the photosensitizer and fluid contained within the container 10 to be exposed to the light emitted from each of the discrete radiation sources (e.g. discrete sources 20 and 30), by continually replacing the exposed fluid at the light-fluid interface with fluid from other parts of the bag not yet exposed to the light. Such mixing continually brings to the surface new fluid to be exposed to light.

The movement of both the support platform 25 and/or the radiation sources 26 and 36 may be controlled by control unit 11. The control unit 11 may also control the rate of light emission.

In a preferred embodiment each discrete light source 20 and 30 emits a peak wavelength of light to irradiate the fluid contained in bag 10. The peak wavelength of light emitted by each discrete light source is selected to provide irradiation of a sufficient intensity to activate both the photosensitizer in a pathogen inactivation process as well as to provide sufficient penetration of light into the particular fluid being irradiated, without causing significant damage to the blood or blood components being irradiated. The preferred photosensitizer is riboflavin. To irradiate a fluid containing red blood cells and riboflavin, it is preferred that each discrete light source 20 and 30 be selected to emit light at a peak wavelength of 470 nm. The 470 nm of light used in this invention is close to the optimal wavelength of light to both photolyse riboflavin, and also to enable significant penetration of the fluid containing red blood cells by the light.

Figure 3:
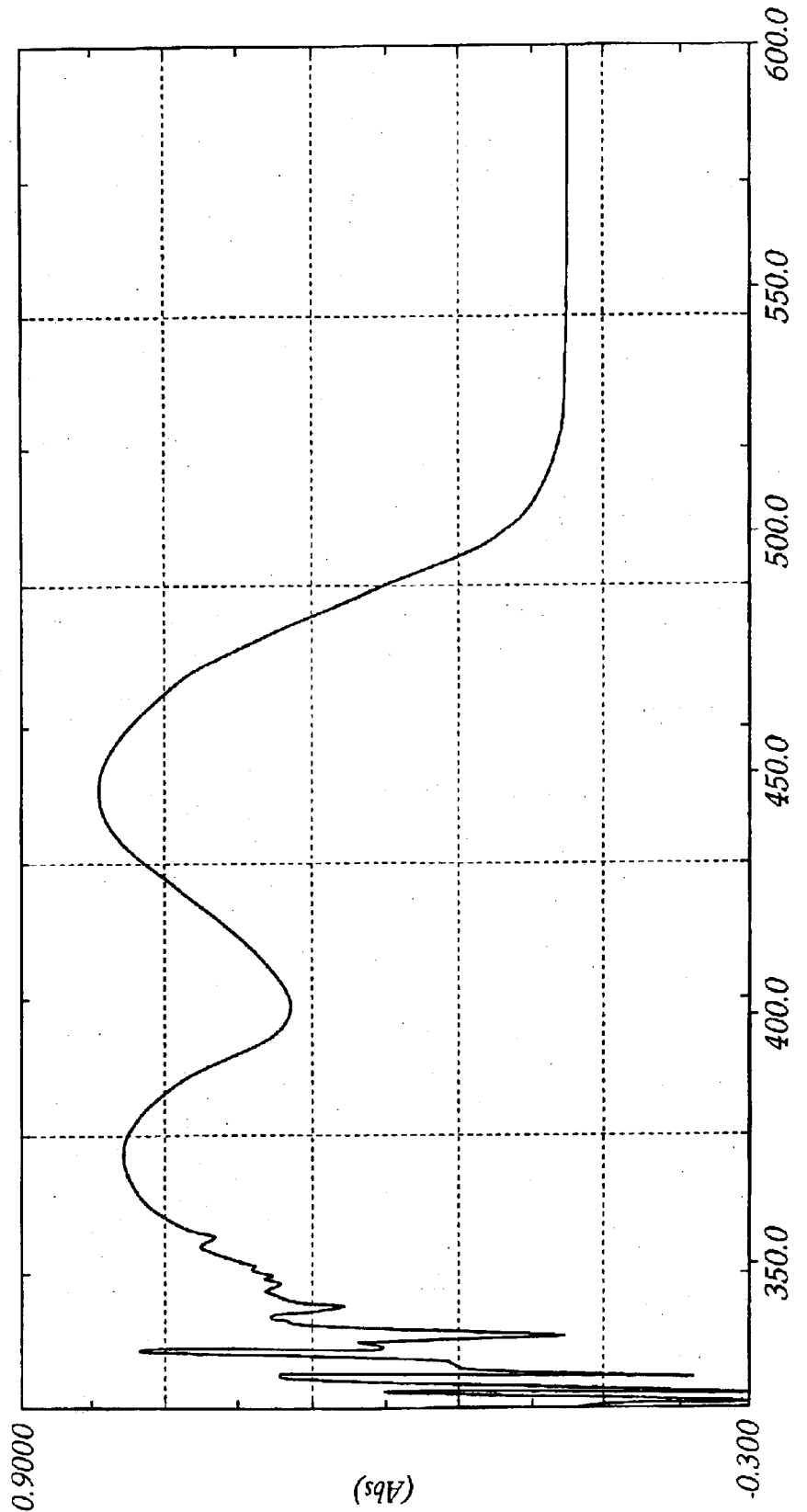
FIG. 3 is a graph depicting the absorption spectrum of riboflavin.

FIG. 3 shows the absorption spectrum of riboflavin. As is seen in FIG. 3, riboflavin is best photolysed at an absorption peak of approximately 450 nm. The absorption spectrum also shows that riboflavin may be successfully photolysed at an absorption peak of approximately 370 nm. A peak wavelength of 370 nm may be used as long as there is minimal absorption by red blood cells and no significant damage to the red blood cells caused by the absorbed light.

Figure 4:
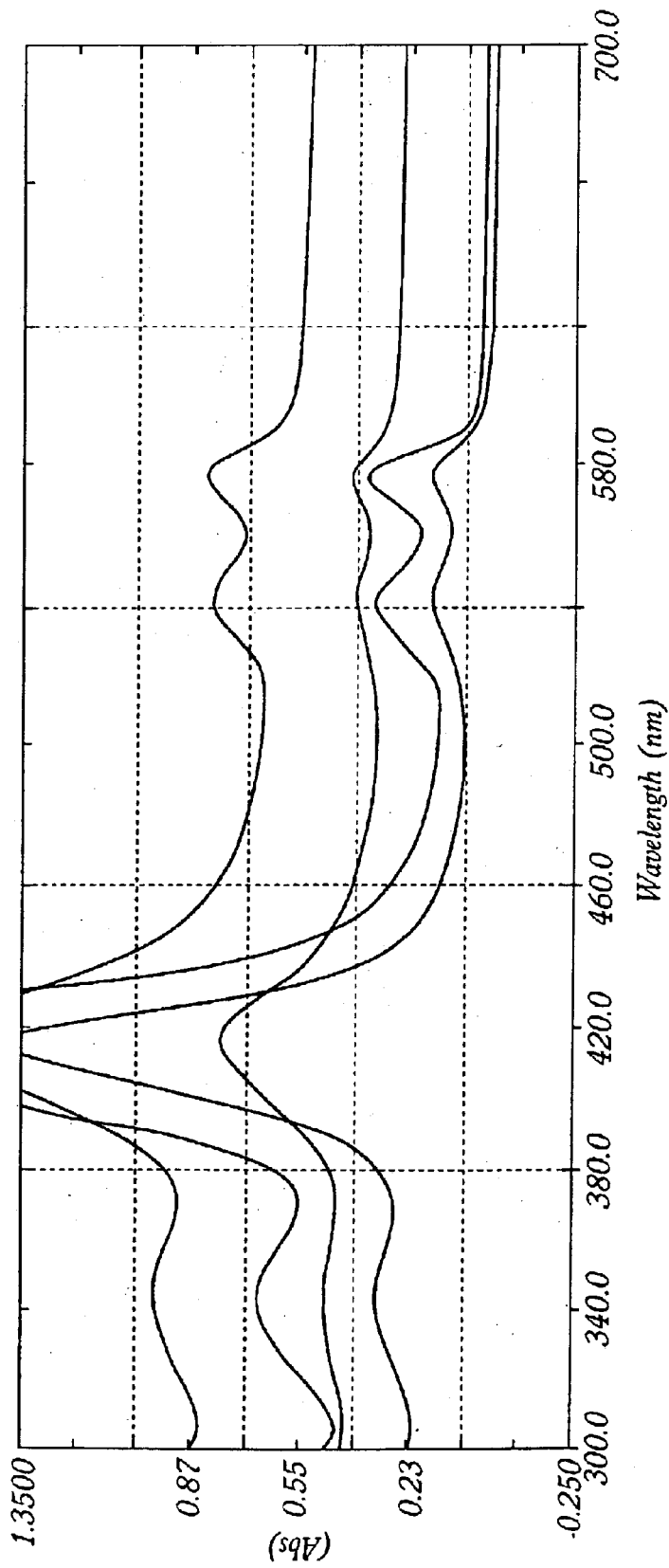
FIG. 4 is a graph depicting the absorption spectrum of hemoglobin at various concentrations.
Figure 12:
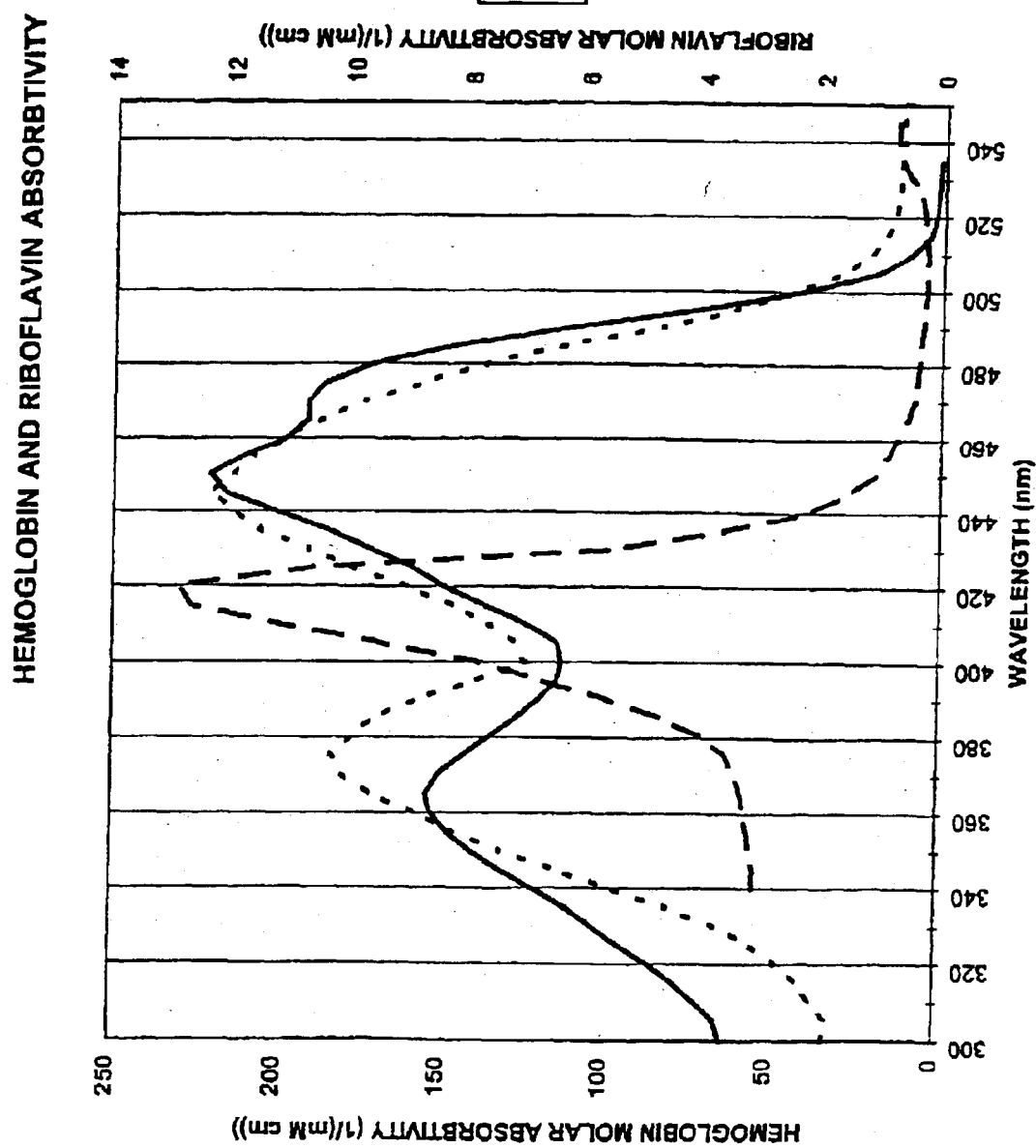
FIG. 12 is a graph depicting the absorption spectrum of hemoglobin and free and bound riboflavin.

FIG. 4 shows the absorption spectrum of hemoglobin at various concentrations. As shown, all concentrations of hemoglobin have absorption peaks around 419 nm. As seen from FIG. 4, a wavelength of 419 nm will be completely absorbed by the red blood cells, significantly decreasing penetration of the light through the cells into the surrounding fluid. At this wavelength, no light will be available to photolyze riboflavin, and therefore, any pathogens contained in the red blood cells will not be reduced. At a wavelength of approximately 470 nm, riboflavin has an absorption peak and the red blood cells will not absorb the light, allowing riboflavin to be photolyzed. This can be seen in the combined absorption peaks of FIGS. 3 and 4, as shown in FIG. 12. As can be seen in FIG. 4 and FIG. 12, a wavelength of 470 nm will not be completely absorbed by red blood cells, and will therefore be able to penetrate into the fluid containing red blood cells. As is seen in FIG. 3 and FIG. 12, a wavelength of approximately 470 nm will photolyse riboflavin, thus enabling pathogen reduction by riboflavin in red blood cells. Such results are unexpected, because as is taught by U.S. Pat. No. 5,527,704, to inactivate fluid containing red blood cells requires light at a wavelength of 690 nm, because red blood cells are transparent to light at this wavelength.

To inactivate pathogens contained in fluid which may contain platelets and/or plasma with a photosensitizer, light having a peak wavelength of around 308 nm may also be used. The range of light between 305-313 nm, and having a peak intensity at around 308 nm when used to irradiate a fluid with a photosensitizer appears to give adequate virus kill and does not produce large scale protein damage to platelets. 308 nm of light also appears to prevent platelet aggregation.

Figure 5:
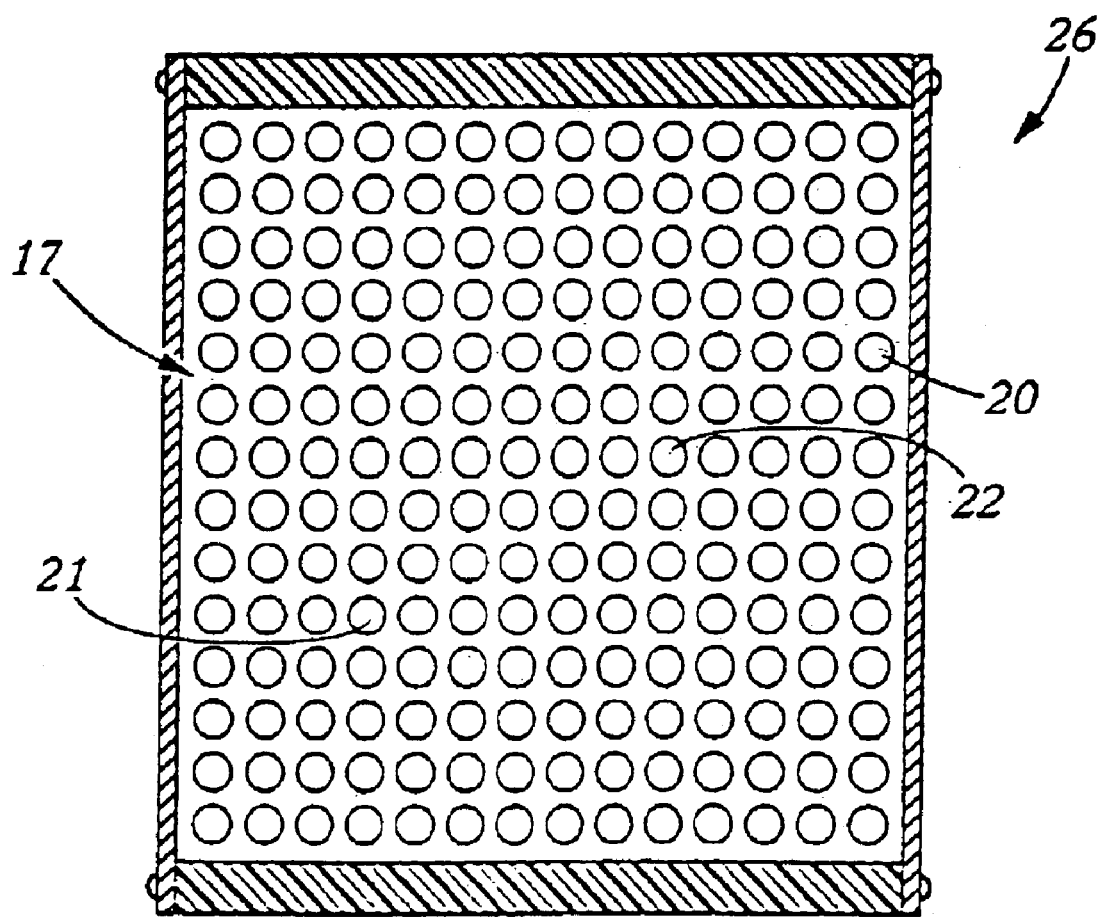
FIG. 5 is a plan view of an array of LEDs that may be used in the present invention.

As shown in FIG. 5, each radiation source 26 may consist of a bank or array of a plurality of discrete LEDs devices. LED devices 20, 21 and 22 are self-contained emitters of radiation. Each LED emits a single color of light when an electrical current is applied. Each of the LED devices in the array 26 may also emit light in the same peak wavelength, which for red blood cells is preferably selected to be around approximately 470 nm, and for platelets is preferably selected to be around approximately 308 nm.

The discrete radiation sources or lights may be arranged in banks or arrays containing multiple rows of individual lights, or may be arranged in a single row (not shown). As shown in FIG. 5, if LED devices are used, a plurality of discrete LED devices may be arranged in multiple rows. The lights may also be staggered or offset from each other (not shown). If a bank or an array of LED lights is located in both the top and the bottom of the irradiation chamber 55 (see FIG. 1), or in a vertical orientation as described above, each bag or container 10 containing fluid to be irradiated will be exposed to light on both the top and the bottom surfaces (or on both sides of the bag if in a vertical orientation). A reflective surface 17 (like that shown in FIG. 1) may also be part of the array.

One or more light sources may be used in the irradiation apparatus, depending on the output required to substantially inactivate viruses which may be present in the blood product, and without substantially damaging the blood component being irradiated.

As described above, the lights used in this invention may be LED devices or other narrow bandwidth sources such as excimer light sources. LEDs are advantageous because they emit light in a very narrow spectrum. Emitting light in a narrow spectrum may be beneficial to the blood product being irradiated because all non-useful wavelengths of light which might damage the blood or blood component being irradiated are eliminated. LED devices are available from any one of a number of companies. Some companies that manufacture LED devices useful in this invention are Cree, Inc. (Durham, N.C., USA); Nichia, Co. (Tokushima, JP); Kingbright, Corp. (City of Industry, Calif., USA) and Lumileds Lighting, LLC (San Jose, Calif., USA). In this invention, LEDs which emit light in the blue color spectrum and emit light at a peak wavelength of approximately 470 nm are most preferred for inactivating pathogens that may be contained in red blood cells. Excimer light sources or LEDs which emit light at a peak wavelength of approximately 308 nm are most preferred for irradiating pathogens that may be contained in platelets and/or plasma.

Figure 6:
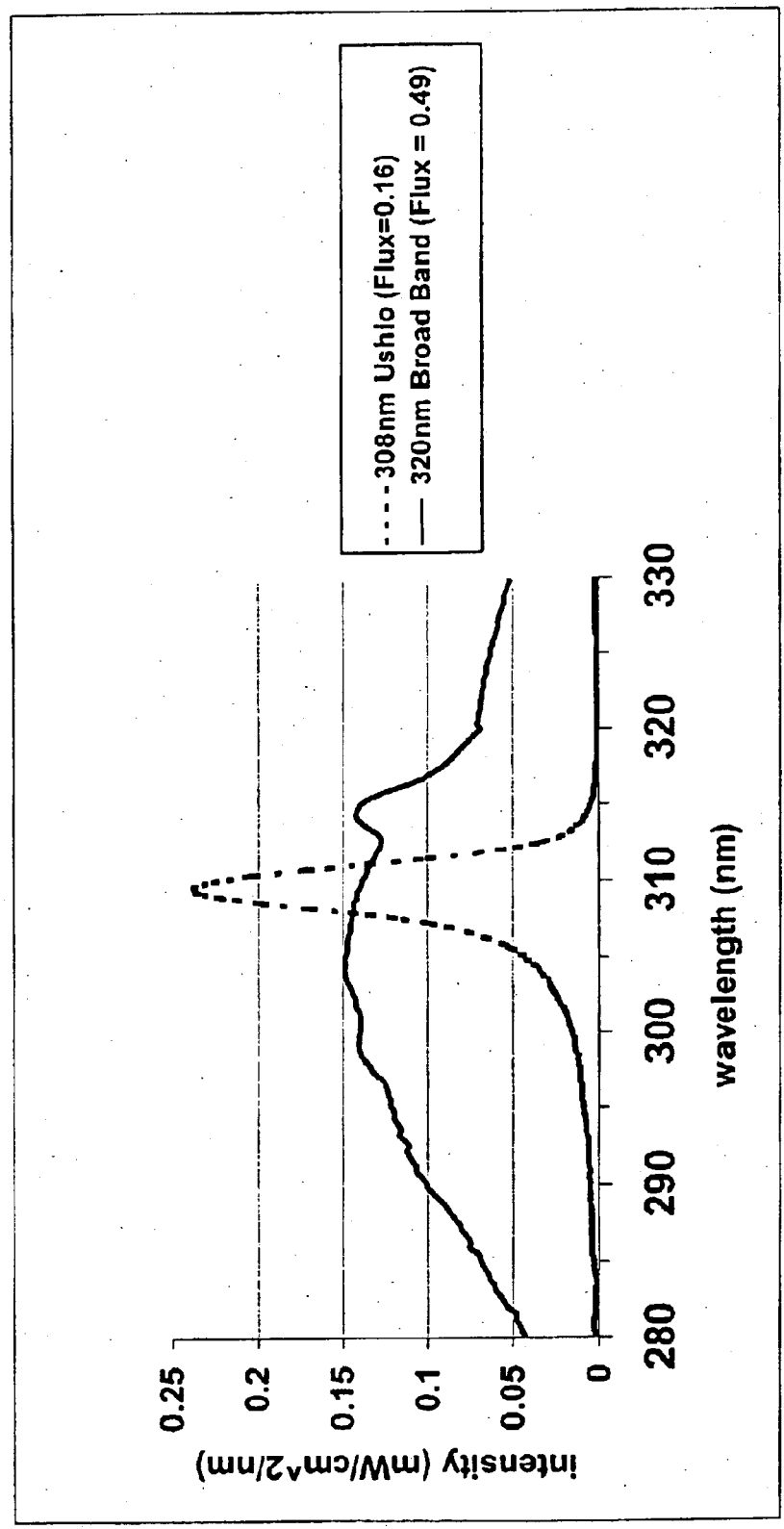
FIG. 6 is a graph depicting the light spectrum of one type of fluorescent bulb which may be used in the present invention as compared to a broad band type of bulb.

One type of excimer light source which may be used in the present invention are lights which emit at a peak wavelength of 308 nm (available from Ushio Corp.). As can be seen from the light spectrum shown in FIG. 6, the Ushio bulbs have a peak wavelength at approximately 308 nm, as compared to 320 nm broadband fluorescent bulbs, which generate light over a much wider spectrum. It should be noted that although Ushio bulbs are described, any light bulbs which emit light at a peak wavelength of 308 nm may be used.

One Ushio bulb produces a flux of around 0.04 $J/cm^2/min$ while two bulbs provide a flux of around 0.11 $J/cm^2/min$. This is compared to the full output of 320 nm fluorescent bulbs which produce a flux of around 0.45 $J/cm^2/min$. To irradiate platelets at an energy level of 7 $J/cm^2$, one Ushio bulb requires 175 minutes of irradiation, while two bulbs require 64 minutes of irradiation. Three Ushio bulbs require irradiation for 24.1 minutes, while four Ushio bulbs require 14 minutes of irradiation. Two banks of four bulbs of broad spectrum 320 nm fluorescent bulbs require 15.5 minutes.

Figure 8:
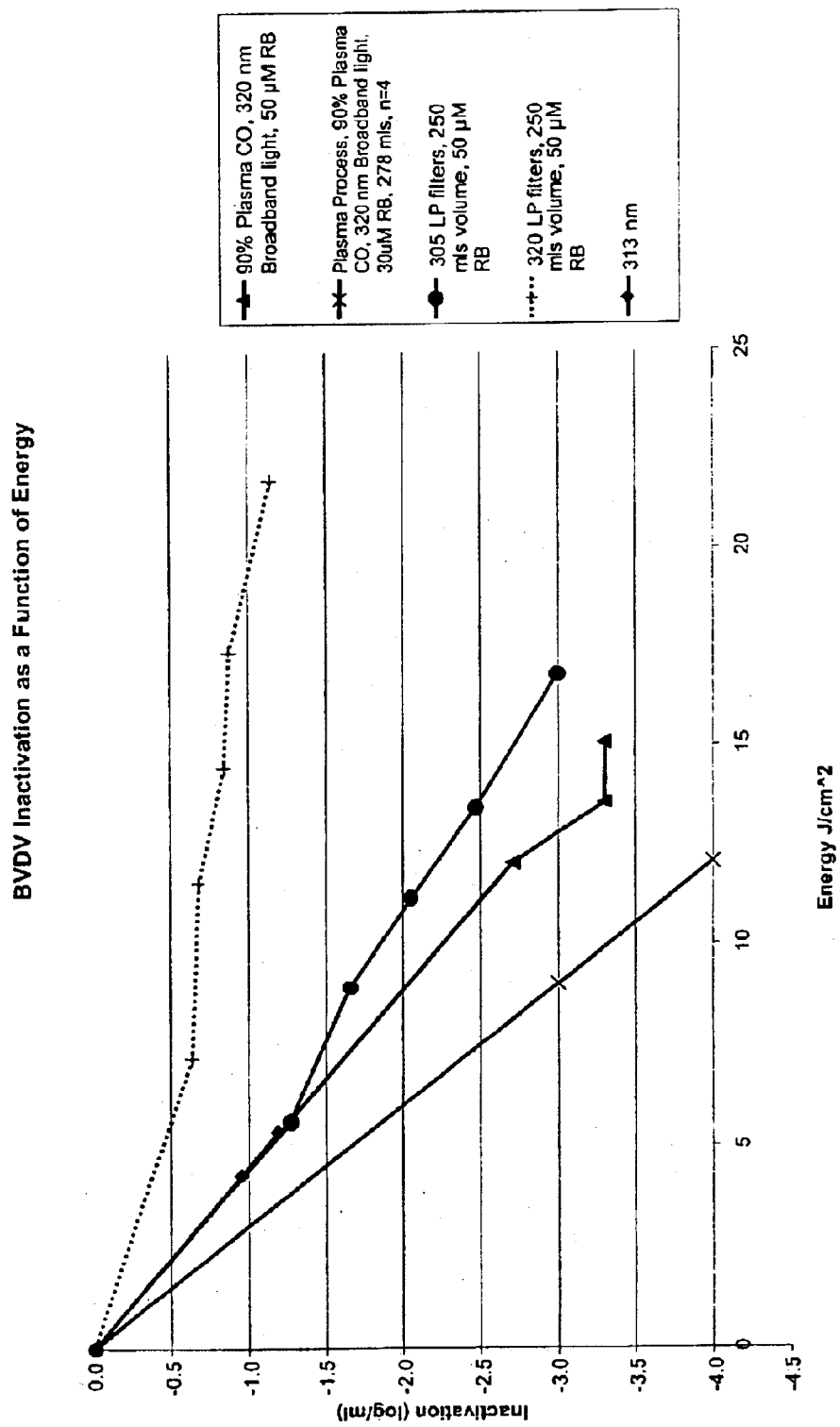
FIG. 8 is another graph comparing virus inactivation as a function of energy.
Figure 11:
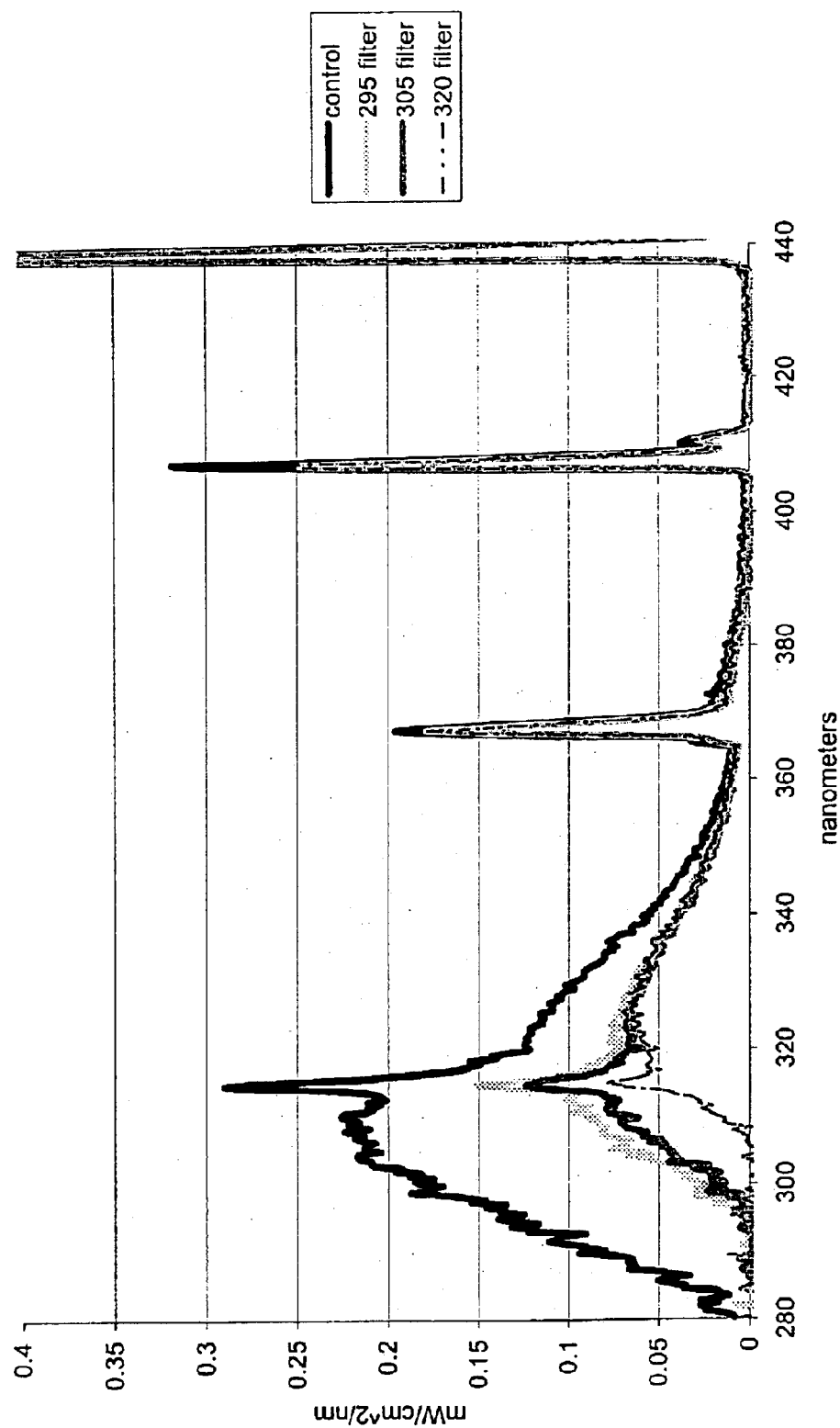
FIG. 11 is a graph depicting the spectral data of 320 nm broadband light used with filters.

To determine the most effective wavelengths of light to substantially reduce pathogens in platelets and plasma without causing substantial damage to the blood components, long pass (LP) filters were initially employed. The spectral data of broad spectrum 320 nm lights which were subjected to filters which filter out light below a certain wavelength are shown in FIG. 11. A 305 LP filter, when applied to light from a 320 nm broadband source will filter out wavelengths below 305 nm. A 320 LP filter will filter out wavelengths below 320 nm. A 295 LP filter will filter out wavelengths below 295 nm. As shown in FIG. 8, light at wavelengths of 320 nm or above provide poorer viral kill as compared to light at wavelengths below 320. As seen in FIG. 8, although the use of a 305 LP filter substantially curtails the range of wavelengths delivered, viral kill appears to be much greater than that achieved using higher wavelengths of light. Therefore, the wavelengths which are not filtered out are most significant for viral kill. FIG. 8 also demonstrates that light emitted in a very narrow range around 313 nm may also be used to substantially reduce pathogens in both plasma and platelets. This graph shows that in plasma (and by analogy in platelets), the amount of virus kill tracks with a given energy dose. Furthermore, light in the 313 nm range appears to follow the amount of viral kill produced by light in the lower range (308 nm).

Figure 7:
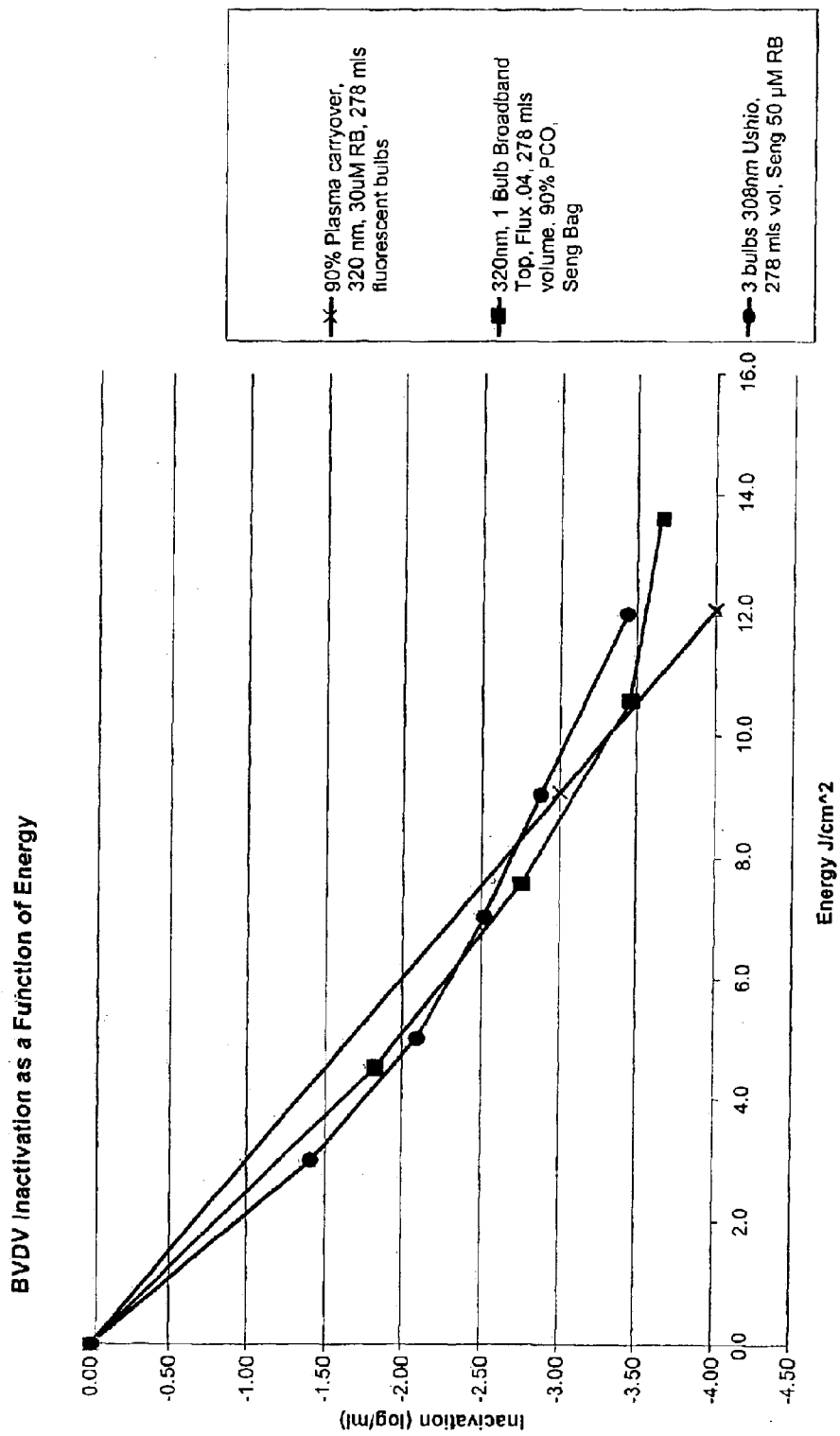
FIG. 7 is a graph comparing virus inactivation as a function of energy.

FIG. 7 is a graph comparing BVDV inactivation in plasma as a function of energy. The conditions used to substantially reduce virus in plasma are analogous to the conditions used to substantially reduce virus in platelets. BVDV was spiked into a 278 mL solution containing 90% plasma carryover. Riboflavin was added at a concentration of between 30–50 $\mu$M. Virus kill achieved using a broadband source of light having a peak wavelength of 320 nm was compared to kill achieved using a narrow bandwidth source with a peak wavelength of 308 nm and kill achieved using a broad spectrum of 320 nm light. As shown, light emitting peaks at 308 nm provided substantially the same amount of viral kill as light emitted from a broad spectrum 320 nm light source, indicating that 308 nm light is very efficient at kill.

Based on the results from the above studies, the quality of platelets irradiated with peak wavelengths as compared to broad spectrum light was studied over five days of storage. 30–50 $\mu$M riboflavin was added to platelets and irradiated at 7 $J/cm^2$ for 14, 15, 24 or 122 minutes, depending on the flux produced by each type of bulb and the number of bulbs used. Platelet quality was measured using common measures of platelet quality such as % Extended Shape Change (ESC), P-selectin, lactate production, and pH. Use of peak wavelengths of light to reduce pathogens in platelets does not appear to damage platelets to the same extent as light having a broad spectrum. This is illustrated in FIGS. 9a–d which show that the cell quality achieved with light having a wavelength of 308 nm resulted in better platelet cell quality, possibly indicating that the additional wavelengths of light that hit the cells from the broad spectrum sources may be damaging.

Figure 9A:
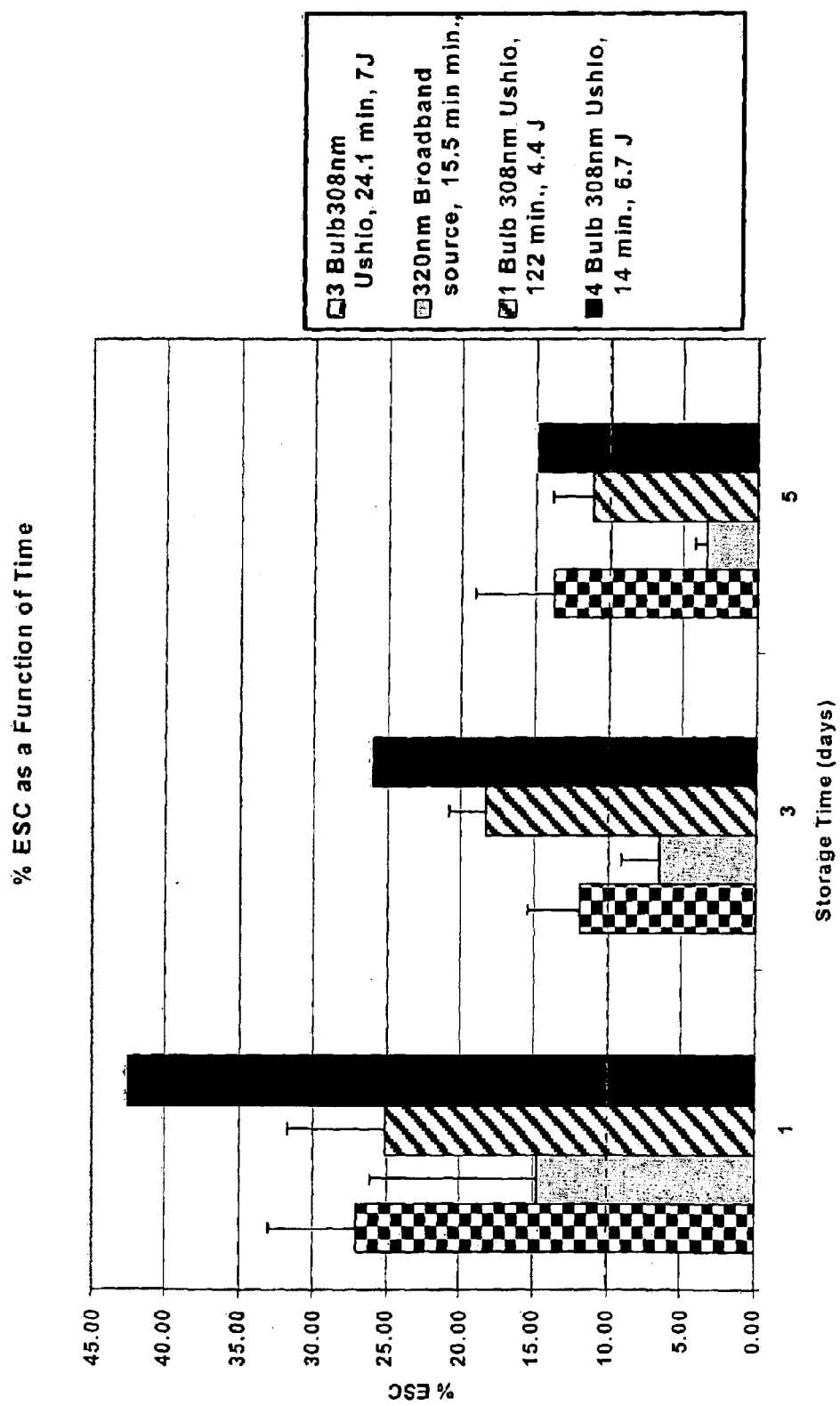
FIG. 9a is a graph depicting the percentage of extended shape change of platelets irradiated with 308 nm of light as compared to broad spectrum light over five days of storage.

FIG. 9a is a graph of the percentage of extended shape change of platelets over five days of storage. Extended shape change is a measure of platelets ability to respond to agonists. Irradiation of platelets with 308 nm Ushio bulbs appears to maintain a higher percentage of ESC as compared to platelets irradiated with broad spectrum 320 nm bulbs.

Figure 9B:
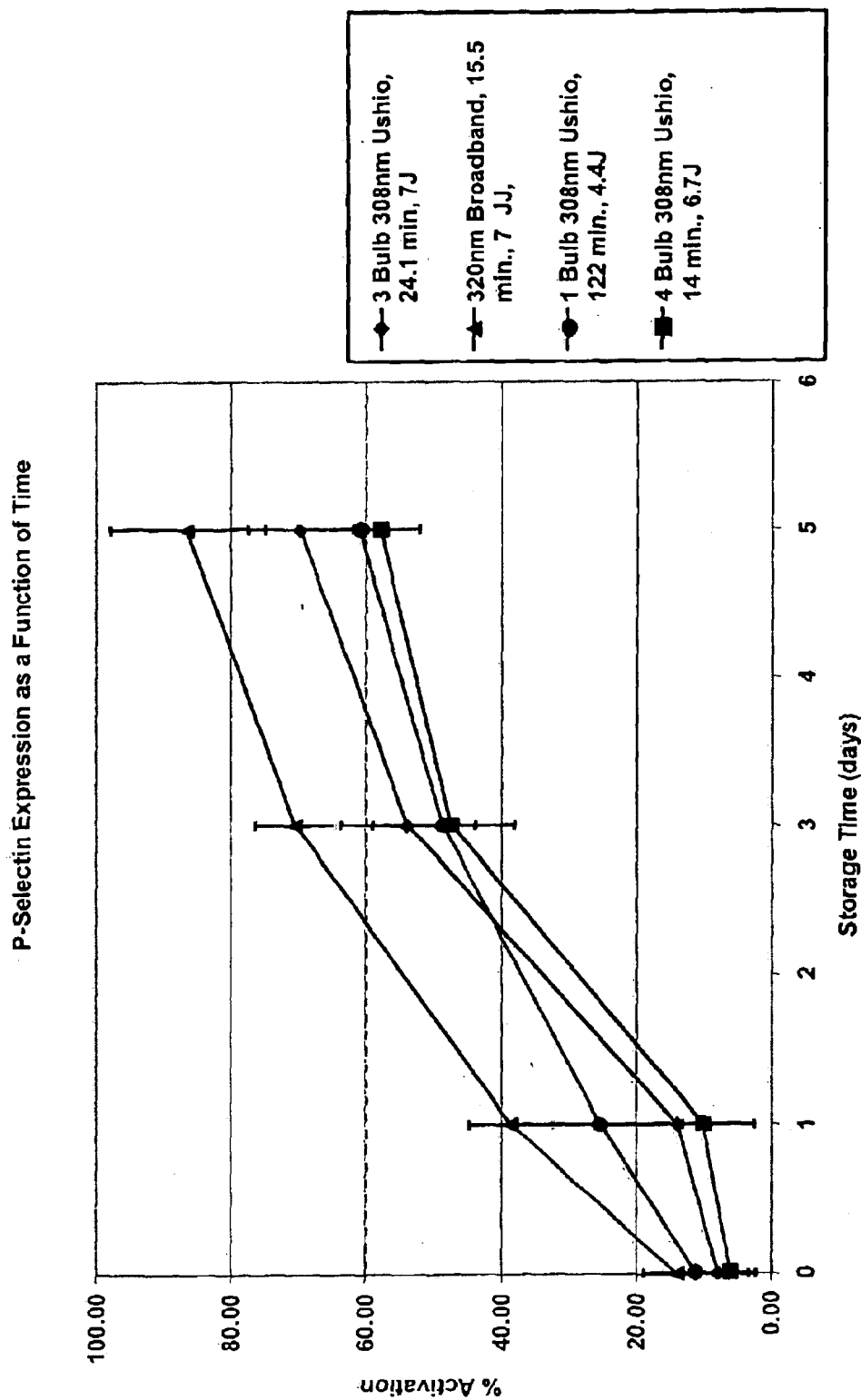
FIG. 9b is a graph depicting the expression of P-selectin by platelets irradiated with 308 nm of light as compared to broad spectrum light over five days of storage.

FIG. 9b is a graph showing P-selectin expression as a function of time. P-selectin is a marker which appears on the surface of platelets when platelets are in an activated state. Platelets which are activated are more likely to aggregate together than non-activated platelets. The occurrence of aggregation has been correlated with removal of platelets from the circulation system and hence have short survival times in the body of a recipient when treated platelets are infused. It appears from FIG. 9b that irradiation using broad spectrum light causes platelets to become more activated than platelets irradiated with light at a peak wavelength of 308 nm.

Figure 9C:
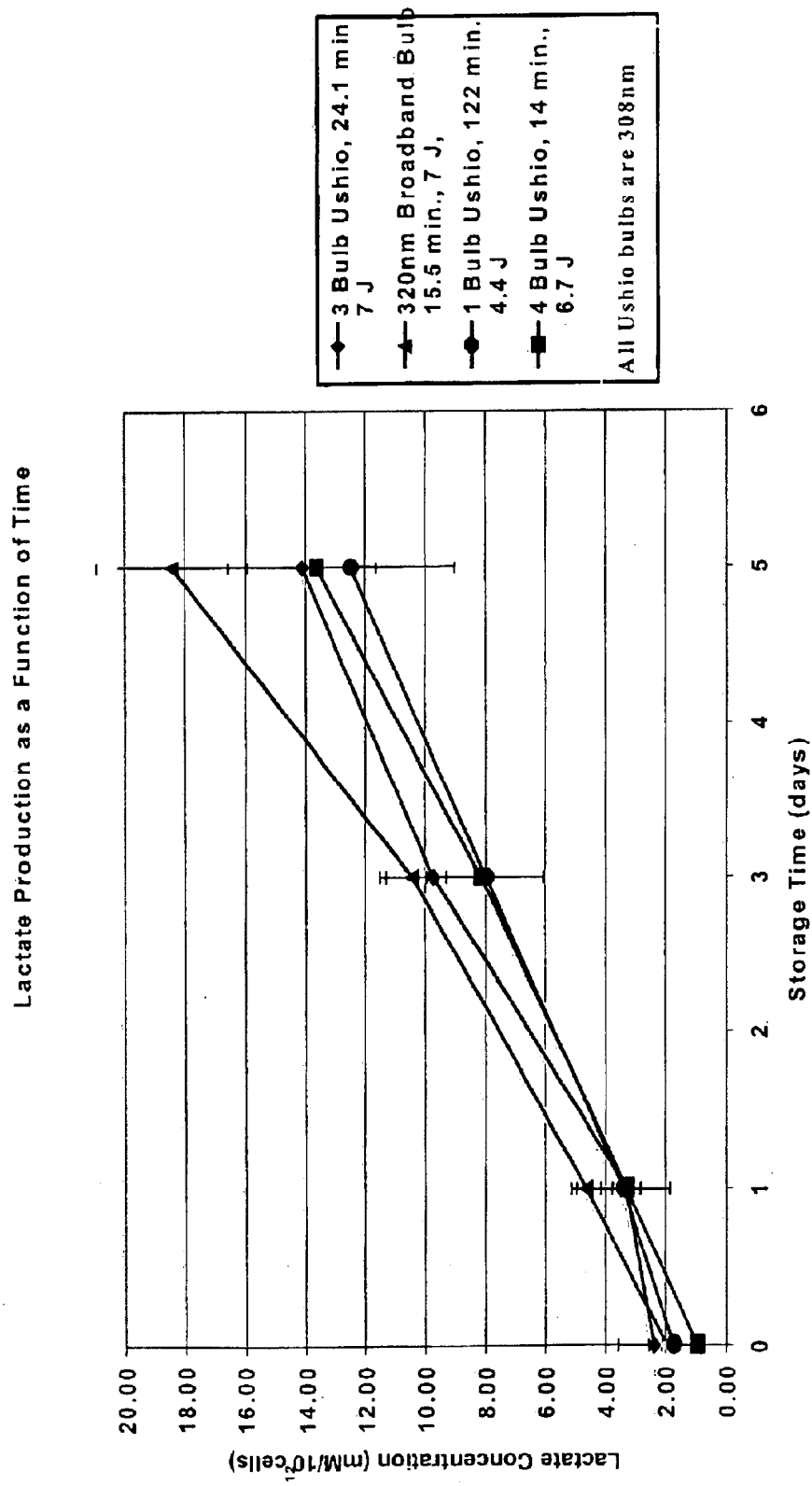
FIG. 9c is a graph depicting the production of lactate by platelets irradiated with 308 nm of light as compared to broad spectrum light over five days of storage.

FIG. 9c shows the production of lactate by platelets during storage. It has been observed that irradiated platelets have suppressed mitochondrial function. If the mitochondria of platelets is suppressed by UV light, platelets are unable to create ATP (cellular energy) through aerobic respiration. If platelets are unable to create energy through aerobic respiration, they will create energy through an alternative pathway called the glycolysis pathway. One metabolite produced by the glycolysis pathway is lactate or lactic acid. Lactic acid buildup within cells causes the pH of the solution to drop. Such a drop in pH causes decreased cell quality during storage. As shown in FIG. 9c, platelets irradiated with broad spectrum light produced lactate at a much higher rate than platelets irradiated with light at a peak wavelength of 308 nm.

Figure 9D:
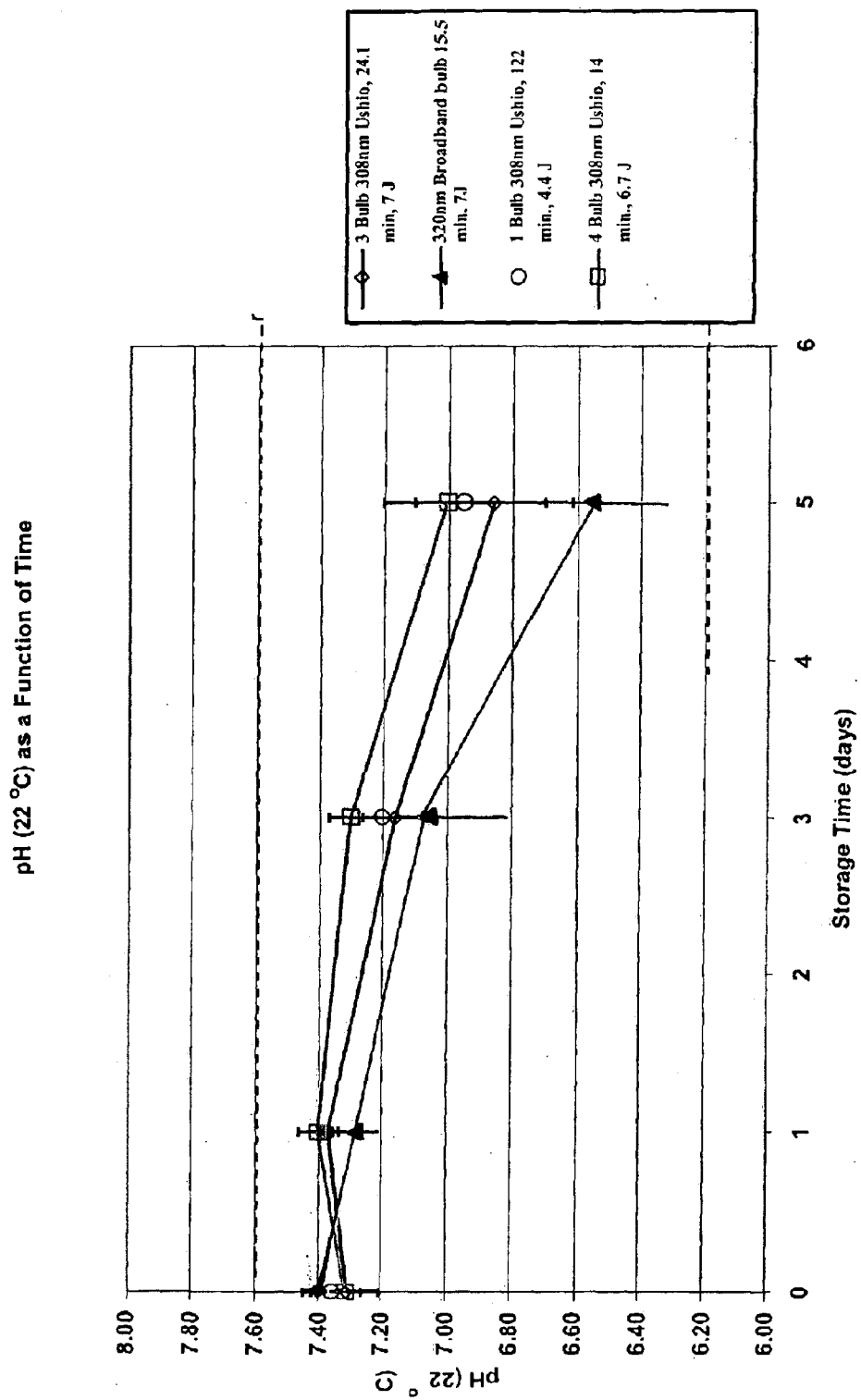
FIG. 9d is a graph depicting the pH of platelets irradiated with 308 nm of light as compared to broad spectrum light over five days of storage.

FIG. 9d is a graph measuring the drop in pH of irradiated platelets over the course of five days. Drops in the pH of platelets during storage is indicative of a decrease in the quality of stored platelets. Platelets which were irradiated with broad spectrum light suffered a greater drop in pH over five days of storage than did platelets irradiated with light at 308 nm.

Although Ushio bulbs are given as one example of bulbs which could be used in the present invention, it should be noted that any type of bulbs, either fluorescent or LEDs which emit light at a peak wavelength between 305–313 nm may be used. Filters which filter out undesired wavelengths of light may also be used to obtain the desired peak wavelength.

If desired, the light sources 20 and 30 may be pulsed. Pulsing the light may be advantageous because the intensity of light produced by the light sources may be increased dramatically if the lights are allowed to be turned off and rested between light pulses. Pulsing the light at a high intensity also allows for greater depth of light penetration into the fluid being irradiated, thus allowing a thicker layer of fluid to be irradiated with each light pulse.

Figure 10:
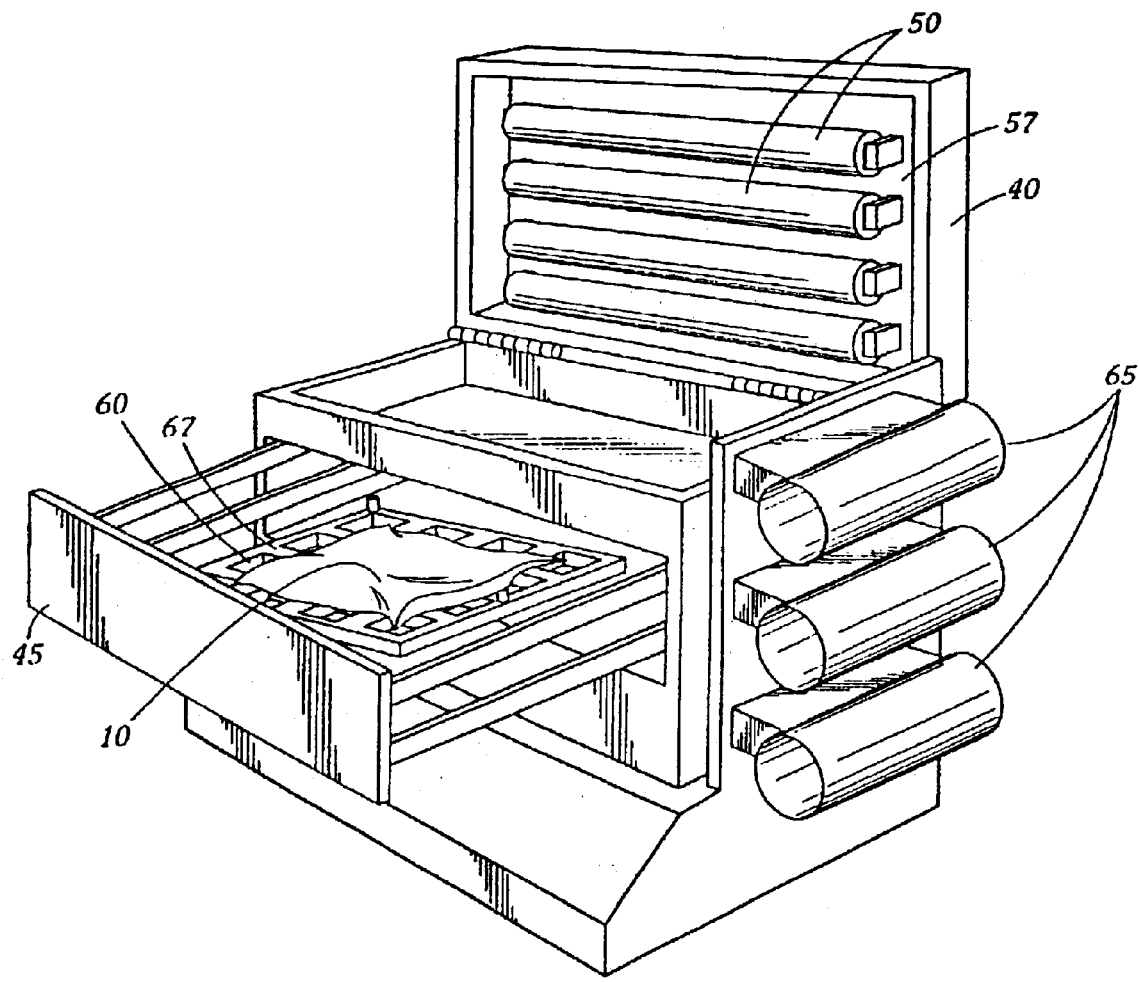
FIG. 10 is another embodiment of a treatment chamber which may be used in the present invention.

FIG. 10 shows an alternative embodiment of an irradiation or treatment chamber to be used with the present invention. A bank of light sources 50 which emit peak wavelengths of light and which may or may not be capable of being pulsed, may be located within the top of the irradiation chamber extending from lid 40. Although not shown in FIG. 10, a bank of lights may also be located in the bottom of the irradiation chamber as well. A reflective surface 57 is shown as part of the inner surface of lid 40, however, reflective surface 57 or another one or more surfaces (not shown) may be located anywhere within the radiation chamber as introduced above.

The lid 40 is capable of being opened and closed. During exposure of the bag 10 containing the fluid to be irradiated to the light sources, the lid 40 is in a closed position (not shown). To add or remove the bag 10 containing the fluid to be irradiated from the irradiation chamber, a drawer 45 located on the front of the irradiation chamber may be disposed in an open position (as shown). During the irradiation procedure, the drawer 45 is placed in a closed position (not shown).

The light sources 50 as shown in FIG. 10, may be fluorescent or incandescent tubes, which stretch the length of the irradiation chamber, or may be a single light source which extends the length and width of the entire chamber (not shown). The LEDs shown in FIG. 5 may also be used in this embodiment.

As shown in FIG. 10, the support platform 67 may be located within and/or forming part of drawer 45. The support platform 67 may contain gaps 60 or holes or spaces within the platform 67 to allow radiation to penetrate through the gaps directly into the container 10 containing fluid to be irradiated.

A cooling system may also optionally be included. As shown in FIG. 10, air cooling using at least one fan 65 may be preferred but it is understood that other well-known systems can also be used. Although not shown in FIG. 10, the method may also include the use of temperature sensors and other cooling mechanisms where necessary to keep the temperature below temperatures at which desired proteins and blood components in the fluid being irradiated are damaged. Preferably, the temperature is kept between about 0° C. and about 45° C., more preferably between about 4° C. and about 37° C., and most preferably about 28° C.

Although described primarily with reference to a stand alone irradiation device used to irradiate individual bags (batch process), peak wavelengths of light may be used to irradiate blood or blood components in a flow-through irradiation system as well, without departing from the scope of the present invention.

What is claimed is:

1. A method for inactivating pathogens in a fluid containing red blood cells comprising;
   adding a photosensitizer to the fluid to form a mixture, and
   exposing the mixture of the fluid and the photosensitizer to light having a peak wavelength of approximately 470 nm.

2. The method of claim 1 wherein the step of exposing further comprises pulsing the light.

3. The method of claim 1 wherein the photosensitizer is an endogenous photosensitizer.

4. The method of claim 1 wherein the photosensitizer is an isoalloxazine.

5. The method of claim 1 wherein the photosensitizer is riboflavin.

6. The method of claim 1 further comprising;
   mixing the fluid and photosensitizer during the exposing step to expose the majority of the fluid to the light.

7. A method for inactivating pathogens in a fluid containing platelets comprising;
   adding a photosensitizer to the fluid to form a mixture, and
   exposing the mixture of the fluid and the photosensitizer to light within an approximate range of between 305–313 nm.

8. A method of claim 7 wherein the step of exposing further comprises exposing the mixture to light having a peak wavelength at 308 nm.

9. The method of claim 7 wherein the exposing step further comprises exposing the mixture to pulsed light at the peak wavelength.

10. The method of claim 7 wherein the photosensitizer is an endogenous photosensitizer.

11. The method of claim 7 wherein the photosensitizer is an isoalloxazine.

12. The method of claim 7 wherein the photosensitizer is riboflavin.

13. The method of claim 7 further comprising: filtering out all light except light in the range of between 305–313 nm.

14. The method of claim 13 wherein the step of filtering comprises filtering out all light in the UV spectrum except light having a peak wavelength of approximately 308 nm.

15. The method of claim 13 wherein the step of filtering comprises filtering out all light in the UV spectrum except light having a peak wavelength of approximately 313 nm.

16. The method of claim 7 wherein the light is pulsed light.

17. A treatment chamber for inactivating pathogens in a fluid containing red blood cells and a photosensitizer comprising:

at least one radiation emitting source emitting radiation at a peak wavelength of approximately 470 nm;

a support platform for holding the fluid containing red blood cells and photosensitizer to be irradiated; and a control unit for controlling the radiation emitting source.

18. The treatment chamber of claim 17 wherein the radiation emitting source is capable of being pulsed.

19. The treatment chamber of claim 18 wherein the control unit further moves the support platform in coordination with the radiation pulses.

20. The treatment chamber of claim 17 wherein the support platform is capable of movement in multiple directions within the treatment chamber.

21. The treatment chamber of claim 20 wherein the control unit further controls the movement of the support platform.

22. The treatment chamber of claim 17 wherein the support platform is made of photopermeable material.

23. The treatment chamber of claim 17 wherein the chamber further comprises at least one reflective surface.

24. The treatment chamber of claim 17 wherein the support platform includes a reflective surface.

25. The treatment chamber of claim 17 wherein the radiation emitting source further comprises an array containing a plurality of discrete lights.

26. The treatment chamber of claim 25 wherein the array containing a plurality of discrete lights further comprises a plurality of LEDs.

27. The treatment chamber of claim 26 wherein the plurality of LEDs are blue.

28. A treatment chamber for inactivating pathogens in a fluid containing platelets and a photosensitizer comprising:

at least one radiation emitting source emitting radiation at a peak wavelength of approximately 308 nm;

a support platform for holding the fluid containing platelets and photosensitizer to be irradiated; and a control unit for controlling the radiation emitting source.

29. The treatment chamber of claim 28 wherein the radiation emitting source is capable of being pulsed.

30. The treatment chamber of claim 29 wherein the control unit further moves the support platform in coordination with the radiation pulses.

31. The treatment chamber of claim 28 wherein the support platform is capable of movement in multiple directions within the treatment chamber.

32. The treatment chamber of claim 31 wherein the control unit further controls the movement of the support platform.

33. The treatment chamber of claim 28 wherein the support platform is made of photopermeable material.

34. The treatment chamber of claim 28 wherein the chamber further comprises at least one reflective surface.

35. The treatment chamber of claim 28 wherein the support platform is made of a reflective surface.

36. A method of irradiating a fluid containing platelets comprising the steps of:

adding an amount of photosensitizer to the fluid necessary to inactivate any pathogens contained in the fluid;

exposing the fluid and photosensitizer to light at a wavelength of approximately 308 nm; end mixing the fluid and photosensitizer during the exposing step to expose the majority of the fluid to the light.

37. A method of irradiating rod blood cells in a fluid contained within a photopermeable bag comprising the steps of:

adding riboflavin to the bag in an amount necessary to inactivate any pathogens contained in the fluid:

exposing the bag containing at least the fluid and riboflavin to a peak wavelength of light; and mixing the contents of the bag during the exposing step.

38. A method of irradiating a blood product comprising the steps of:

a) adding an amount of photosensitizer necessary to inactivate any pathogens contained in the blood product;

b) pulsing a radiation source having a peak wavelength of light of approximately 470 nm to expose the blood product and photosensitizer to radiation at the peak wavelength;

c) pulsing the radiation source off to stop exposure of the blood product and photosensitizer to radiation;

d) mixing the blood product and photosensitizer during the step of pulsing the radiation source off; and e) repeating steps b), c) and d).

* * * * *